United States Patent
Park et al.

(10) Patent No.: US 6,738,666 B1
(45) Date of Patent: May 18, 2004

(54) DETECTION OF ORTHOSTATIC HYPOTENSION USING POSITIONAL DATA AND CROSS-CHECK DATA

(75) Inventors: Euljoon Park, Stevenson Ranch, CA (US); Kerry Bradley, Glendale, CA (US)

(73) Assignee: Pacesetter, Inc., Sylmar, CA (US)

(*) Notice: Subject to any disclaimer, the term of this patent is extended or adjusted under 35 U.S.C. 154(b) by 387 days.

(21) Appl. No.: 10/002,615

(22) Filed: Nov. 1, 2001

(51) Int. Cl.[7] ............................................. A61N 1/365
(52) U.S. Cl. ......................................................... 607/18
(58) Field of Search ............................... 607/17, 18, 19, 607/20, 21, 22, 23, 24, 9, 2, 14, 27

(56) References Cited

U.S. PATENT DOCUMENTS 6,625,493 B2 * 9/2003 Kroll et al. .................... 607/17

2003/0045910 A1 * 3/2003 Sorensen et al. ............. 607/23
2003/0078623 A1 * 4/2003 Weinberg et al. .............. 607/9

* cited by examiner

Primary Examiner—George Manuel

(57) ABSTRACT

An implantable cardiac stimulation device is programmed to administer pacing therapy in response to a postural change in a patient's position and a confirmation of that postural change using a cross-check parameter. The stimulation device is equipped with a position sensor to sense a position parameter indicative of when a patient changes from a horizontal position to an upright position. The stimulation device further monitors a cross-check parameter that is affected or modulated by position changes. When the position sensor indicates a postural change and the cross-check parameter confirms this change as being sufficient to induce orthostatic hypotension, the device administers cardiac pacing therapy to the patient.

44 Claims, 5 Drawing Sheets

DETECTION OF ORTHOSTATIC HYPOTENSION USING POSITIONAL DATA AND CROSS-CHECK DATA

TECHNICAL FIELD

The present invention generally relates to methods and systems for providing cardiac pacing therapy. More particularly, the invention concerns methods and implantable stimulation devices to detect onset of orthostatic hypotension.

BACKGROUND

When an individual changes from a horizontal or supine position to a sitting or standing position, the cardiovascular system must make frequent and rapid adjustments to blood pressure and heart rate. When such adjustments are not accomplished, orthostatic hypotension occurs. Orthostasis means upright posture, and hypotension means low blood pressure. Thus, orthostatic hypotension describes the effects caused by low blood pressure when changing from a lying to upright position. Orthostatic hypotension is defined as a decrease of at least 20 mm Hg in systolic blood pressure when an individual moves from the horizontal to upright position.

The symptoms of orthostatic hypotension include dizziness, faintness, or lightheadedness that appear when standing. Other symptoms that often accompany orthostatic hypotension include chest pain, trouble holding urine, impotence, and dry skin from loss of sweating. Some patients with severe orthostatic hypotension are severely incapacitated.

Ideally, a cardiac stimulation device would detect conditions that might give rise to orthostatic hypotension and rapidly transition to an increased pacing rate to counteract the effects of orthostatic hypotension. Unfortunately, detecting the onset of orthostatic hypotension is not an easy task. Moving from a horizontal position to an upright position takes place in a very short time frame. For effective treatment, the cardiac stimulation device should be able to detect the conditions accurately and administer the pacing therapy in a very short period of time.

Accordingly, there is a need for improved detection techniques for accurately detecting the onset of orthostatic hypotension to allow for timely administration of pacing therapy.

SUMMARY

An implantable cardiac stimulation device is programmed to administer pacing therapy in response to a postural change in a patient's position and a confirmation of that postural change using a cross-check parameter. The pacing therapy is an increase in the cardiac pacing rate to counteract effects of orthostatic hypotension.

In the described implementation, the cardiac stimulation device is equipped with a position sensor to sense a position parameter indicative of when a patient changes from a horizontal position to an upright position, such as when moving from a sleeping or reclined posture to a sitting or standing posture. One example of a position sensor is a 3D accelerometer that detects bodily orientation in three dimensions.

The cardiac stimulation device is further equipped with additional sensors and a data acquisition system to monitor at least one cross-check parameter that is affected or modulated by changes in the patient's position. The cross-check parameter is used to confirm that a postural change of the sort that might induce orthostatic hypotension did occur. In one implementation, the cross-check parameter is an evoked response parameter (ERP) functionally related to the evoked response amplitude (ERA) measured in the right ventricle. The device computes a delta ERP ($\Delta$ERA) as a function of the ERP and the moving average of the ERP. By examining changes in the $\Delta$ERP during approximately the time when the postural change is detected by the position sensor, the device can confirm or deny occurrence of a significant postural change.

The cardiac stimulation device includes a processor operably coupled to the position sensor, other sensors, and data acquisition system. The processor is programmed to determine when to administer cardiac pacing therapy to the patient based on the position parameter and the cross-check parameter. For instance, the processor applies an increased pacing rate effective to treat orthostatic hypotension when the device (1) detects a postural change from a horizontal position to an upright position and (2) confirms that postural change via the cross-check parameter, such as changes in the ERP.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

An implantable cardiac stimulation device is programmed to administer pacing therapy in response to a postural change in a patient's position and a confirmation of that postural change using a cross-check parameter. The stimulation device is equipped with a position sensor to sense a position parameter indicative of when a patient changes from a horizontal position to an upright position. The stimulation device further monitors a cross-check parameter that is affected or modulated by position changes. One example of this cross-check parameter is an evoked response parameter (ERP) functionally related to the evoked response amplitude (ERA) measured in the right ventricle. The ERA is modulated by the end-diastolic volume in the ventricle, which is indirectly affected by changes in the patient's position. When the position sensor indicates a postural change and the cross-check parameter confirms this change, the device administers cardiac pacing therapy to the patient.

Exemplary Stimulation Device

The techniques described below are intended to be implemented in connection with any stimulation device that is configured or configurable to stimulate or shock a patient's heart.

Figure 1:
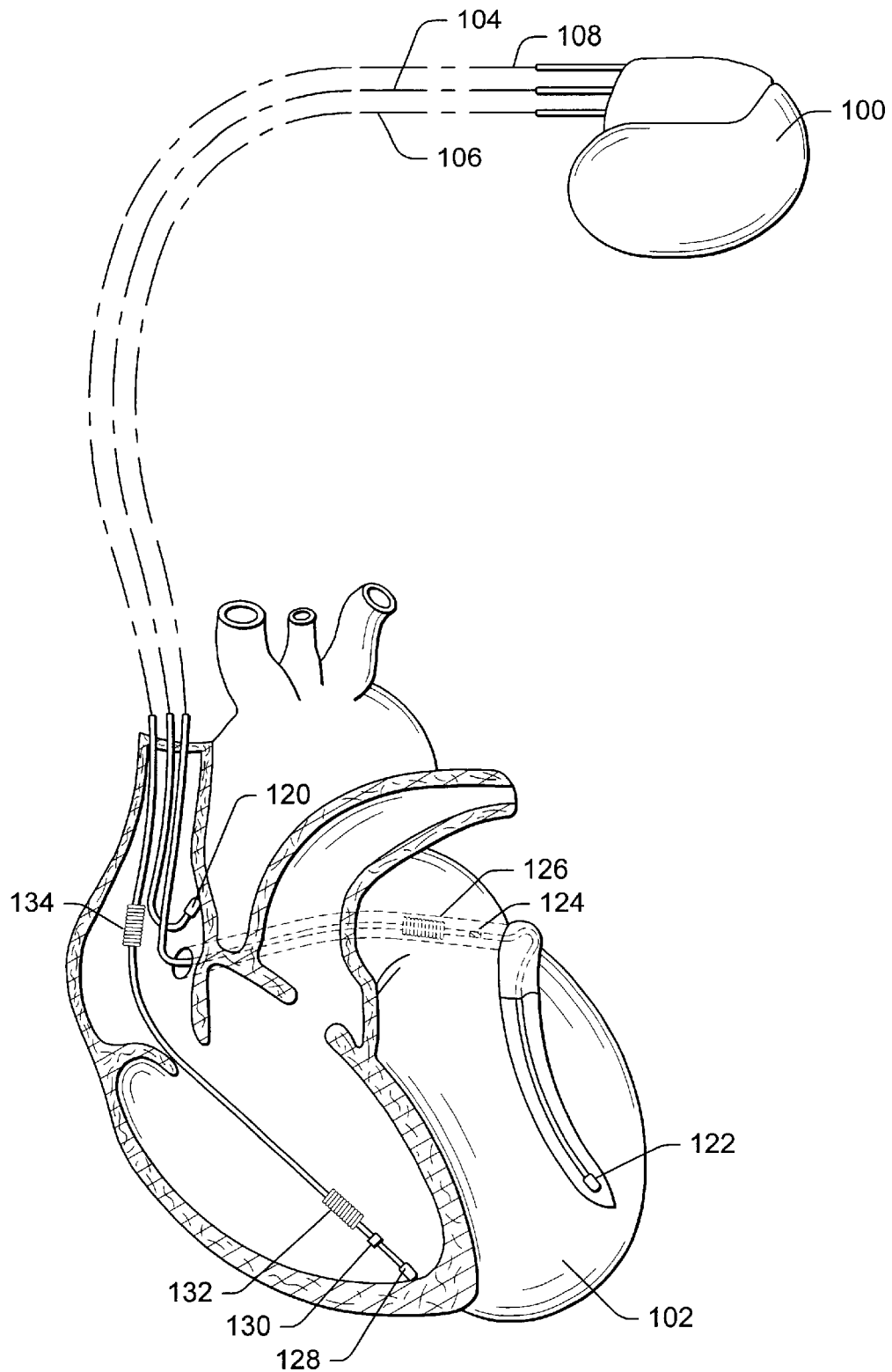
FIG. 1 is a simplified diagram illustrating an implantable stimulation device in electrical communication with at least three leads implanted into a patient's heart for delivering multi-chamber stimulation and shock therapy.

FIG. 1 shows an exemplary stimulation device 100 in electrical Communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having at least an atrial tip electrode 120, which typically is implanted in the patient's right atrial appendage.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using at least a left ventricular tip electrode 122, left atrial pacing therapy using at least a left atrial ring electrode 124, and shocking therapy using at least a left atrial coil electrode 126.

Stimulation device 100 is also shown in electrical communication with the patient's heart 102 by way of an implantable right ventricular lead 108 having, in this implementation, a right ventricular tip electrode 128, a right ventricular ring electrode/sensor 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Figure 2:
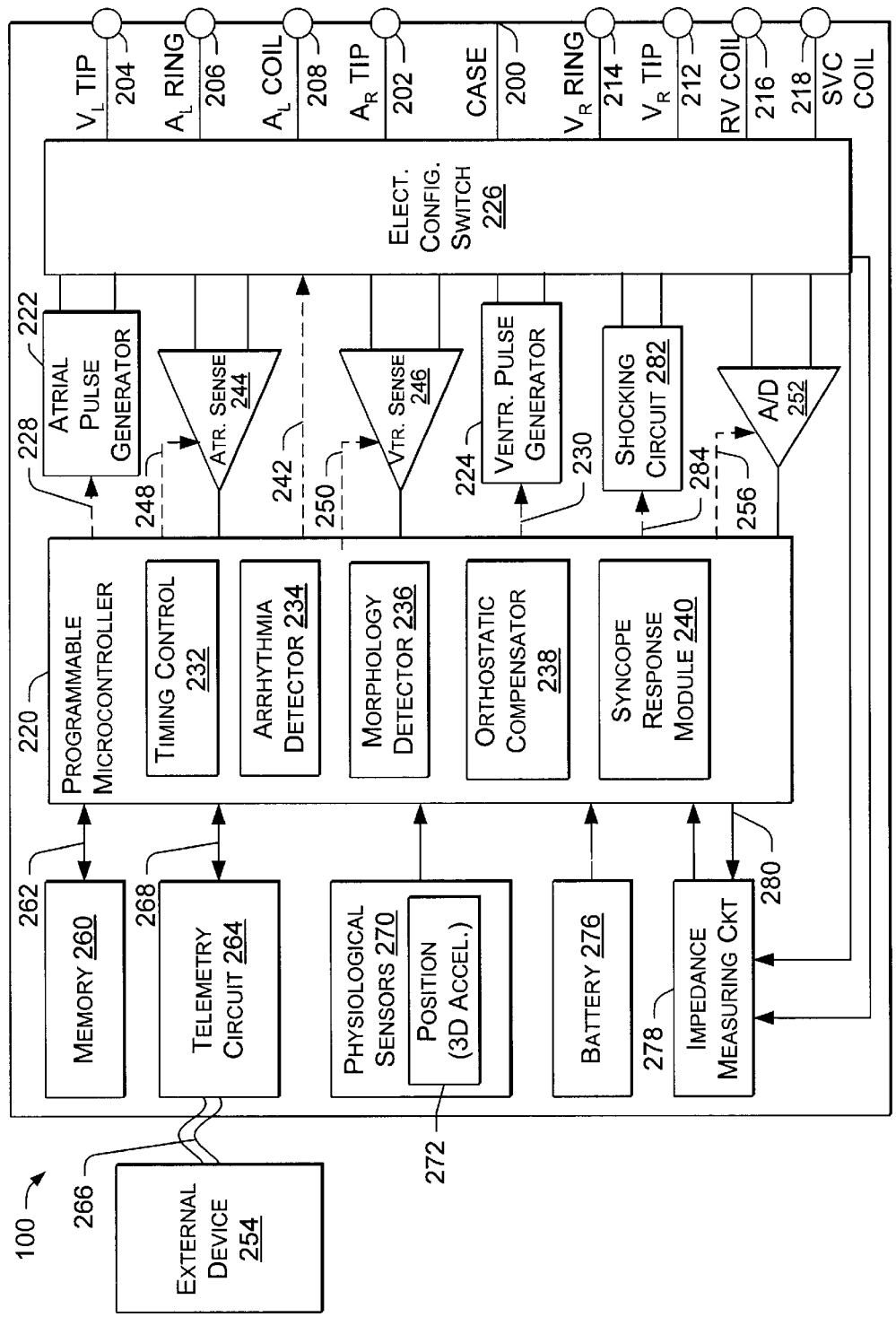
FIG. 2 is a functional block diagram of a multi-chamber implantable stimulation device illustrating basic elements that are configured to provide cardioversion, defibrillation, and pacing stimulation in four chambers of the heart. The implantable stimulation device is further configured to detect onset of orthostatic hypotension and apply therapy to reduce the effects of orthostatic hypotension.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal ($A_R$ TIP) 202 adapted for connection to the atrial tip electrode 120. To achieve left chamber sensing, pacing, and shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular ring electrode 122, the left atrial tip electrode 124, and the left atrial coil electrode 126, respectively.

To support right chamber sensing, pacing, and shocking, the connector further includes a right ventricular tip terminal ($V_R$ TIP) 212, a right ventricular ring terminal ($V_R$ RING) 214, a right ventricular shocking terminal (RV COIL) 216, and an SVC shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, an orthostatic compensator 238, and a syncope response module 240. These components can be utilized by the stimulation device 100 for determining desirable times to administer various therapies, including those to reduce the effects of orthostatic hypotension and vasovagal syncope, as will become more apparent below. The components 234–240 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low 3 amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224, respectively, in a demand fashion in response to the absence or presence of cardiac activity in the appropriate chambers of the heart. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

Advantageously, the data acquisition system 252 may be coupled to the microcontroller 220, or other detection circuitry, for detecting an evoked response from the heart 102 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include one or more physiologic sensors 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses. While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate and/or minute ventilation, pH of blood, ventricular gradient, and so forth. The physiological sensors 270 may further include a pressure sensor that is coupled to detect RV pressure that is sensed by a sensor located at ring 130, which can perform dual functions of a ring electrode and a pressure sensor.

Generally, the physiological sensors 270 further include sensors for detecting position or postural changes. Any sensor capable of sensing such changes, either directly or indirectly, may be used. In particular, the physiological sensors 270 include an activity or position sensor 272 mounted within the housing 200 of the stimulation device 100 to detect movement in the patient's position. The position sensor 272 may be implemented in many ways, including as a 3D accelerometer, a sensor that detects the earth's magnetic or gravitational fields, a MEMs (micro-electro mechanical) device, and the like. Another sensor that may be used is one that detects activity variance, wherein an activity sensor is monitored diurnally to detect the low variance in the measurement corresponding to the sleep state.

Signals generated by the position sensor 272 are passed to the microcontroller 220 for analysis in determining whether to invoke the orthostatic compensator 238. The microcontroller 220 monitors the sensor signals for changes indicating that the patient has moved from a horizontal position to an upright position. For example, the position sensor may generate a signal with little activity while the patient is sleeping or resting. This inactivity may go on for some time. Then, when the patient wakes and sits up, the position sensor will generate signals indicative of this movement. The microcontroller 220 confirms from the sudden change in sensor output following a prolonged period of inactivity that the patient has indeed sit or stood up, and is not merely bending over. The microcontroller 220 uses this information as one condition for deciding when to invoke the orthostatic compensator 238 to apply cardiac pacing therapy for treating orthostatic hypotension.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 $\mu$A), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected. Accordingly, the device 100 preferably employs lithium/silver vanadium oxide batteries, as is true for most (if not all) current devices.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (up to 0.5 Joules), moderate (0.5–10 Joules), or high energy (11 to 40 Joules), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Orthostatic Hypotension Therapy

Figure 3:
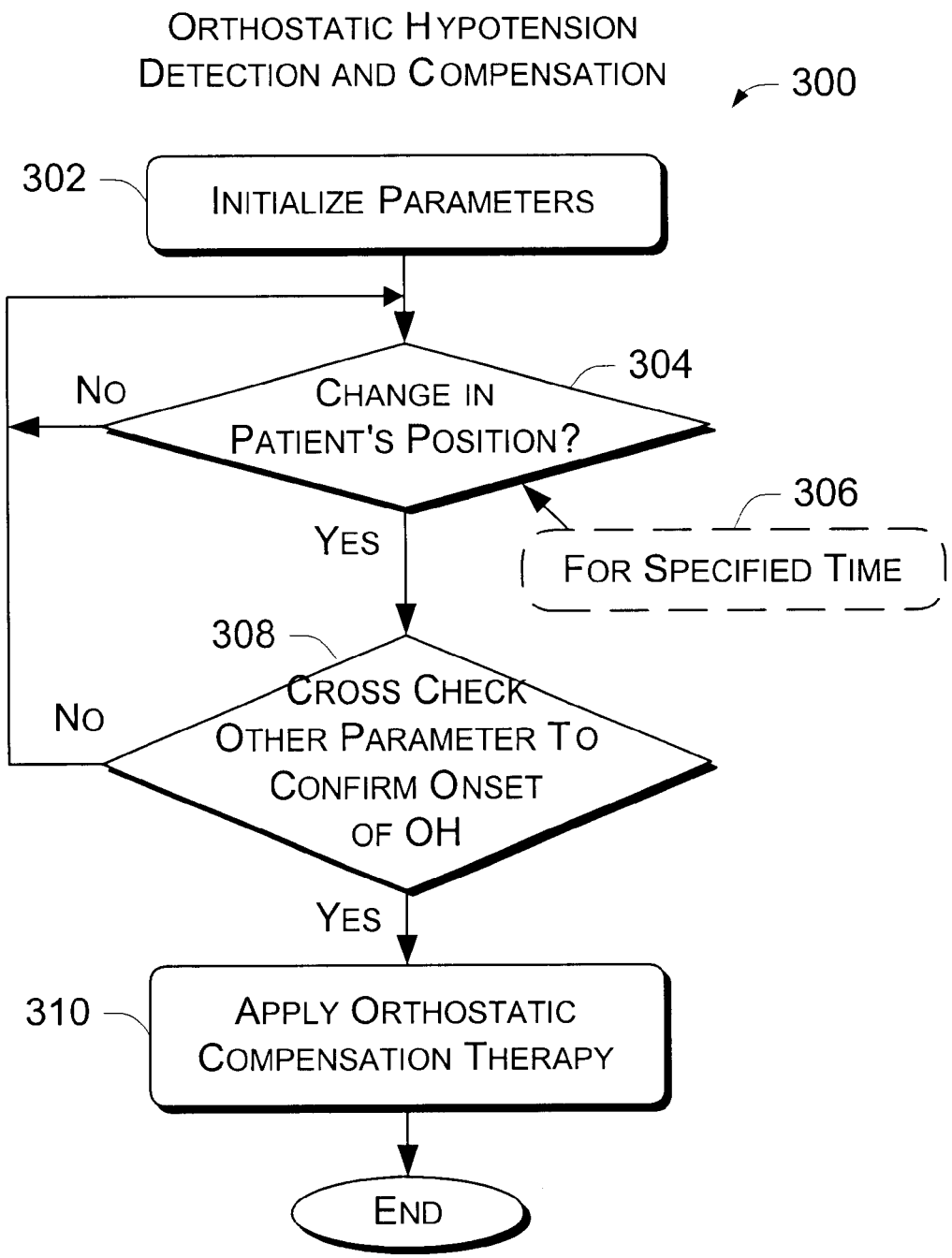
FIG. 3 is a flow diagram of a process to detect conditions that might give rise to orthostatic hypotension and to administer pacing therapy to reduce any effects of orthostatic hypotension.

FIG. 3 shows an exemplary process 300 for detecting conditions that might give rise to orthostatic hypotension and administering pacing therapy to reduce any effects of orthostatic hypotension. The method can be implemented in connection with any suitably configured stimulation device. One specific and non-limiting example of a stimulation device was described above with respect to FIGS. 1 and 2.

In this flow diagram, various algorithmic acts are summarized in individual "blocks". Such blocks describe specific actions or decisions that are made or carried out as the process proceeds. Where a microcontroller (or equivalent) is employed, the flow charts presented herein provide a basis for a "control program" or software/firmware that may be used by such a microcontroller (or equivalent) to effectuate the desired control of the stimulation device. As such, the process 300 is implemented as machine-readable instructions stored in memory that, when executed by a processor, perform the various acts illustrated as blocks.

Those skilled in the art may readily write such a control program based on the flow charts and other descriptions presented herein. It is to be understood and appreciated that the inventive subject matter described herein includes not only stimulation devices when programmed to perform the steps described below, but the software that is configured to program the microcontrollers and, additionally, any and all computer-readable media on which such software might be embodied. Examples of such computer-readable media include, without limitation, floppy disks, hard disks, CDs, RAM, ROM, flash memory and the like.

At block 302, the parameters used in monitoring for onset of orthostatic hypotension are initialized. Such parameters include position information, such as vector data from the three directional axes of the position sensor 272, or time-based position data captured over a period of time, or any other position data indicative of changes in a patient's position. Of particular interest is position data that is used as a benchmark against which the microcontroller is able to detect movement of the patient from a horizontal position to an upright position.

At block 304, the device 100 monitors for changes in a patient's position using the position data output by position sensor 272. More specifically, the microcontroller 220 attempts to detect when the patient changes from a horizontal position to an upright position, particularly following a prolonged period of inactivity while the patient is in the horizontal position. Detection may be based on absolute changes in data, such as through use of an absolute position sensor that detects when the patient has reoriented from a horizontal position to a vertical position. In the absence of a postural change indicative of a horizontal-to-upright movement, the process 300 continues to monitor for position changes in the patient, as represented by the "No" branch from block 304.

To discriminate sudden movements (e.g., bending over) from the desired horizontal-to-upright change, detection in block 304 may involve an additional time factor 306 that limits detection until a specified time period has elapsed. The time period can be programmed to any desired value that differentiates brief position changes from significant postural changes. With time based detection, the device is first able to confirm that the patient is in the horizontal position by noting the lack of change in the position data for a prolonged period of time, which is indicative of sleeping or resting. When the patient subsequently sits or stands up for more that a brief period of time, the device confirms the postural change and returns a condition positive from block 304 (i.e., the "Yes" branch from block 304).

At block 308, the device cross checks another parameter that may be used to ascertain an onset of orthostatic hypotension. Cross-checking a second parameter that is independent of positional data helps guard against situations where the positional data is mistakenly interpreted as causing an onset of orthostatic hypotension (i.e., "false positives"). If the cross-check parameter does not confirm an onset of orthostatic hypotension (i.e., the "No" branch from block 308), the device returns to the base pacing rate. Conversely, if the cross-check parameter confirms the onset of orthostatic hypotension (i.e., the "Yes" branch from block 308), the device 100 applies pacing therapy effective for combating orthostatic hypotension (block 310).

In one implementation, the device 100 utilizes modulation of the evoked response amplitude (ERA) to detect and confirm changes in the postural status of the patient as a way to cross-check whether orthostatic hypotension is beginning to occur. The ERA is modulated by the end-diastolic volume in the ventricle. As the patient assumes an upright posture, there is an immediate decrease in venous return, due to gravitational force on the blood volume and relatively high venous compliance. With less venous return, there is decreased myocardial distension with less end-diastolic volume. The reduced blood mass, relatively thicker ventricular wall around the pacing/sensing electrode, and reduced wall-tension results in an increased ERA.

Figure 4:
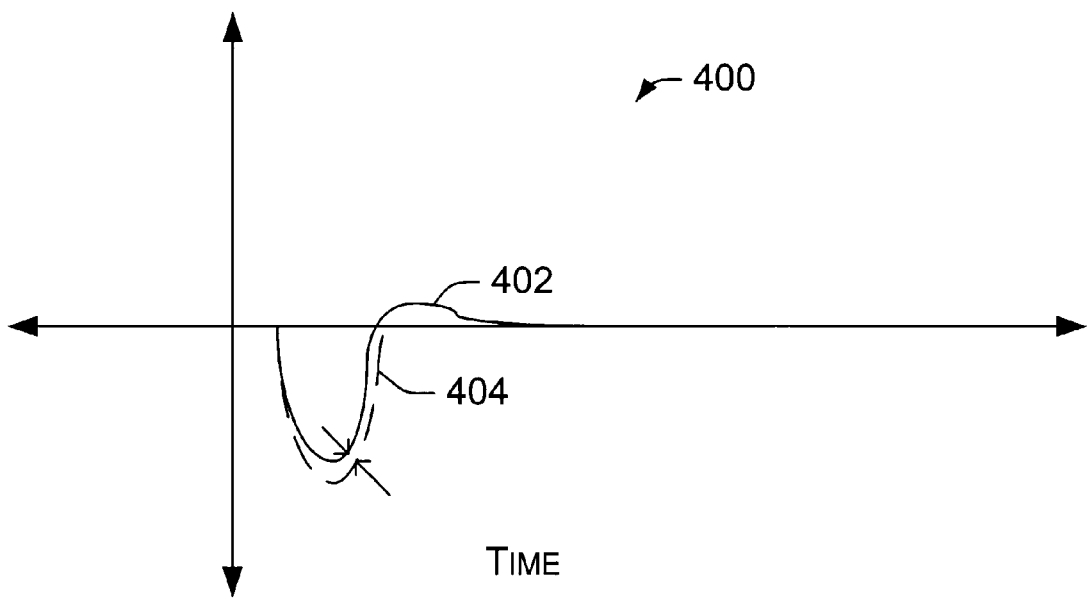
FIG. 4 is a graphical illustration of an evoked response, and demonstrates changes in amplitude as a result of position changes in the patient.

FIG. 4 illustrates a portion of an evoked response waveform 400 monitored in the right ventricle following a pacing pulse (not shown). Change in the evoked response amplitude (ERA) of waveform 400 can be used to confirm an onset of orthostatic hypotension. Base conditions are illustrated as the solid line 402. A broken line 404 illustrates an increased ERA caused by a change in the patient's posture, such as that from a horizontal position to an upright position.

When the orthostatic compensator 238 goes into alert mode, indicating that the patient has been inactive for a meaningful period of time and is either sitting or horizontal, the orthostatic compensator 238 begins monitoring an evoked response parameter that is functionally related to the ERA. The orthostatic compensator 238 computes a short-term moving average of the ERP (e.g., a minimum of 5 beats or more, where more beats would be averaged to eliminate respiratory variations in the ERA). This average is stored in memory 260 and is updated on a beat-by-beat basis. Also, a delta ERP ($\Delta$ERP) is calculated on a beat-by-beat basis. The $\Delta$ERP is calculated as follows:

$$\Delta ERP = ERP(\text{current beat}) - (\text{moving-averaged } ERP).$$

The delta values are also stored in memory 260 for the last few beats (e.g., approximately 10 beats).

When the orthostatic compensator 238 detects a possible change in posture based on signals from the position sensor 272 (e.g., an accelerometer), the orthostatic compensator 238 examines the last few $\Delta$ERP values in memory 260 that correspond to the few beats after the suspected change in posture. If a large positive change in the $\Delta$ERP values is observed, the postural change is confirmed as true and orthostatic compensation therapy is applied at operation 310. Conversely, if no or a small change in the ΔERP is seen, the postural change is confirmed as negative without application of full orthostatic compensation therapy.

It is noted that other cross-check parameters may be used in place of ERA or ERP. Examples of other parameters include stroke volume, a cardiac impedance parameter (e.g., cardiac impedance, first derivative of cardiac impedance, etc.), evoked response integral (also known as the post-depolarization integral or ventricular gradient), ventricular wall thickness, ventricular pressure, atrial evoked response amplitude, atrial evoked response integral, and the like. The atrial ERA is also modulated by postural changes and may be processed similarly and combined with the ventricular measurements (or used independently) to increase the accuracy of the posture detection/cross-checking.

Figure 5:
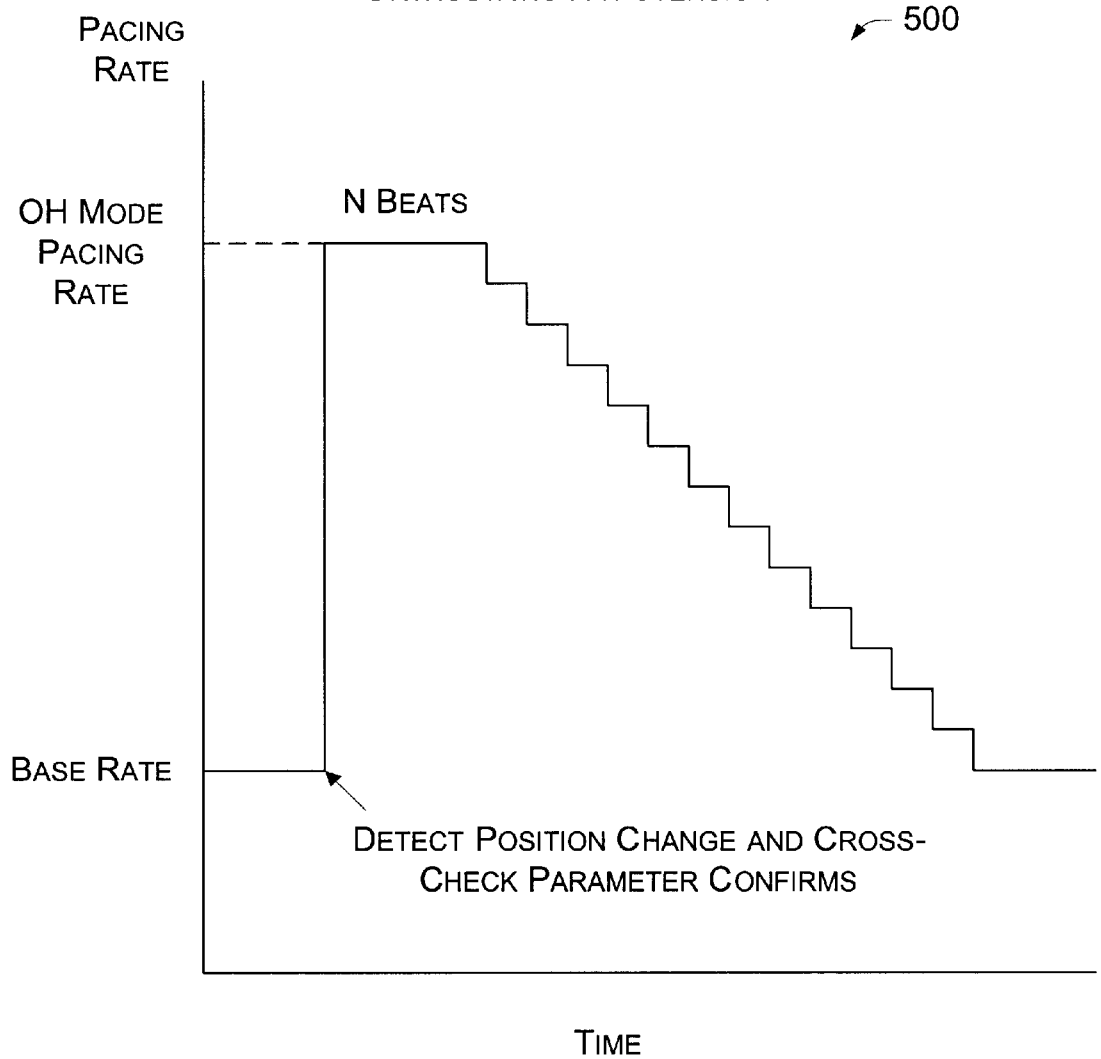
FIG. 5 is a graphical illustration of a pacing therapy effective for treating orthostatic hypotension.

FIG. 5 shows an exemplary pacing therapy 500 that is triggered upon satisfying the position condition, and confirmation by the cross-check parameter. Initially, the pacing rate is at a base rate of, say, 50–70 ppm. When both conditions are met, the pacing rate is adjusted from the base rate to an upper pacing rate programmed into an orthostatic hypotension (OH) mode. As an example, the OH mode pacing rate may be approximately 100 ppm, although these rates are programmable for individual patients. This increased rate is maintained for a programmable number of beats or predetermined time period. The increased pacing rate causes the heart to beat faster, pumping more blood into the system and hence, increasing blood pressure.

After a predetermined period or number of beats, the device 100 systematically begins decreasing the pacing rate toward a reduced rate. The pacing rate reduction is performed gradually over a period of time, as indicated by the step-wise curve of therapy 500 in FIG. 5.

By accurately detecting when a patient sits or stands up from a horizontal position through concurrent confirmation of a cross-check parameter, and rapidly applying therapy, the pacing device 100 is able to reduce or eliminate the effects of orthostatic hypotension. The quick response makes it less likely for the patient to experience dizziness, faintness, or lightheadedness when standing.

It is noted that the above described processes and systems may be used to treat other conditions that are similarly impacted by changes in the patient's posture. For instance, the processes and systems may be used to treat vasovagal syncope.

Conclusion

Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

What is claimed is:

1. A method comprising:
    determining a position parameter indicative of a change in a patient's position;
    determining a cross-check parameter affected at least in part by the change in the patient's position; and
    selectively administering pacing therapy to the patient based on the position parameter and the cross-check parameter.

2. The method of claim 1, wherein the determining a position parameter comprises:
    monitoring position data generated by a position sensor; and
    detecting, from the position data, a change in the patient's position from a horizontal position to an upright position.

3. The method of claim 2, wherein the detecting comprises detecting the change in the patient's position for a specified period of time.

4. The method of claim 1, wherein the determining a cross-check parameter comprises detecting changes in an evoked response amplitude.

5. The method of claim 1, wherein the determining a cross-check parameter is selected from a group of parameters comprising stroke volume, a cardiac impedance parameter, evoked response integral, ventricular wall thickness, ventricular pressure, atrial evoked response amplitude, and atrial evoked response integral.

6. The method of claim 1, wherein the determining a cross-check parameter comprises:
    monitoring an evoked response parameter (ERP) functionally related to an evoked response amplitude (ERA);
    computing a delta ERP (ΔERP) as a function of the ERP and a moving average of the ERP; and
    evaluating the ΔERP computed at approximately a time when the position parameter indicates the change in the patient's position.

7. The method of claim 6, wherein the determining a cross-check parameter further comprises confirming the change in patient's position in response to significant change in the ΔERP.

8. The method of claim 1, wherein the administering comprises increasing a cardiac pacing rate from a first pacing rate to a higher second pacing rate.

9. The method of claim 1, wherein the administering comprises administering a pacing therapy effective to counteract effects of orthostatic hypotension.

10. The method of claim 1, further comprising systematically removing the pacing therapy after a predetermined amount of time.

11. The method of claim 1, wherein the cross-check parameter comprises a first cross-check parameter and further comprising:
    determining a second cross-check parameter affected at least in part by the change in the patient's position; and
    selectively administering pacing therapy to the patient based on the position parameter, the first cross-check parameter, and a second cross-check parameter.

12. One or more computer-readable media having computer-readable instructions thereon which, when executed by a programmable stimulation device, cause the stimulation device to execute the method of claim 1.

13. A method of administering pacing therapy for orthostatic hypotension, comprising:
    detecting a postural change in a patient from a horizontal position to an upright position;
    confirming the postural change using a cross-check parameter; and
    adjusting a cardiac pacing rate from a first pacing rate to a second pacing rate effective to counteract effects of orthostatic hypotension in response to detection of the postural change in the patient's position and confirmation of the postural change via the cross-check parameter.

14. The method of claim 13, wherein the detecting comprises:
    monitoring positional data generated by a 3D accelerometer; and detecting, from the positional data, the change from the horizontal position to the upright position.

15. The method of claim 13, wherein the detecting comprises detecting the change for a specified period of time.

16. The method of claim 13, wherein the confirming comprises detecting changes in an evoked response amplitude.

17. The method of claim 13, wherein the determining a cross-check parameter is selected from a group of parameters comprising stroke volume, a cardiac impedance parameter, evoked response integral, ventricular wall thickness, ventricular pressure, atrial evoked response amplitude, and atrial evoked response integral.

18. The method of claim 13, wherein the confirming comprises:
   monitoring an evoked response parameter (ERP) functionally related to an evoked response amplitude (ERA);
   computing a delta ERP ($\Delta$ERP) as a function of the ERP and a moving average of the ERP; and
   evaluating the $\Delta$ERP computed at approximately a time when the position parameter indicates the change in the patient's position.

19. The method of claim 13, further comprising adjusting the cardiac pacing rate back toward the first pacing rate.

20. The method of claim 13, further comprising adjusting the cardiac pacing rate back toward the first pacing rate after a predetermined amount of time.

21. One or more computer-readable media having computer-readable instructions thereon which, when executed by a programmable stimulation device, cause the stimulation device to execute the method of claim 13.

22. A method comprising:
   detecting a postural change in a patient;
   evaluating an evoked response parameter functionally related to an evoked response amplitude for an indication of the postural change; and
   applying cardiac pacing therapy in response to detection of the postural change that is additionally confirmed by the evoked response parameter.

23. The method of claim 22, wherein the evaluating comprises:
   monitoring the evoked response parameter (ERP);
   computing a delta ERP ($\Delta$ERP) as a function of the ERP and a moving average of the ERP;
   examining the $\Delta$ERP computed at approximately at time when the postural change is detected; and
   in an event that the $\Delta$ERP changes by a predetermined amount, confirming that the postural change did occur.

24. One or more computer-readable media having computer-readable instructions thereon which, when executed by a programmable stimulation device, cause the stimulation device to execute the method of claim 22.

25. A method comprising:
   increasing a pacing rate in a cardiac stimulation device from a first rate to a higher second rate upon (1) detection of a change in patient's position and (2) confirmation of the change using a non-position parameter; and
   subsequently decreasing the pacing rate back toward the first rate.

26. The method of claim 25, wherein the non-position parameter is selected from a group of parameters comprising stroke volume, a cardiac impedance parameter, evoked response integral, ventricular wall thickness, ventricular pressure, atrial evoked response amplitude, and atrial evoked response integral.

27. The method of claim 25, further comprising decreasing the pacing rate after a predetermined period of time.

28. One or more computer-readable media having computer-readable instructions thereon which, when executed by a programmable stimulation device, cause the stimulation device to execute the method of claim 25.

29. A cardiac stimulation device comprising:
   a position sensor to sense a position parameter indicative of changes in a patient's position;
   a processor operably coupled to the position sensor, the processor being configured to determine when to administer cardiac pacing therapy to the patient based on the position parameter and a second cross-check parameter that is affected by the change in the patient's position and is used to confirm a position change sensed by the position sensor; and
   a pacing generator configured to administer the cardiac pacing therapy as directed by the processor.

30. The cardiac stimulation device of claim 29, wherein the position sensor comprises a 3D accelerometer.

31. The cardiac stimulation device of claim 29, wherein the position sensor is configured to sense a change from a horizontal position to an upright position.

32. The cardiac stimulation device of claim 29, wherein the cross-check parameter comprises a ventricular evoked response amplitude.

33. The cardiac stimulation device of claim 29, wherein the cross-check parameter comprises a cross-check parameter is selected from a group of parameters comprising stroke volume, a cardiac impedance parameter, evoked response integral, ventricular wall thickness, ventricular pressure, atrial evoked response amplitude, and atrial evoked response integral.

34. The cardiac stimulation device of claim 29, wherein the processor determines to administer cardiac pacing therapy when the position sensor detects a postural change from a horizontal position to an upright position and the cross-check parameter confirms the postural change.

35. The cardiac stimulation device of claim 34, wherein the pacing generator increases a pacing rate from a first rate to a higher second rate.

36. The cardiac stimulation device of claim 34, wherein the pacing generator generates a pacing rate effective to counteract effects of orthostatic hypotension.

37. The cardiac stimulation device of claim 34, wherein the pacing generator administers the cardiac pacing therapy for a predetermined period of time.

38. An implantable cardiac rhythm management device, comprising:
   position sensing means for sensing a change in a patient's position from a horizontal position to an upright position;
   evaluation means for evaluating a cross-check parameter affected by the change in the patient's position; and
   therapy delivery means, responsive to the position sensing means and the evaluation means, for generating cardiac stimulating pulses at an increased rate effective to treat orthostatic hypotension when the position sensing means senses a postural change from a horizontal position to an upright position and the evaluation means confirms the postural change.

39. The implantable cardiac rhythm management device of claim 38, wherein the evaluation means comprises detecting means for detecting changes in an evoked response amplitude.

40. The implantable cardiac rhythm management device of claim 38, wherein the therapy delivery means systematically reduces the pulse rate following treatment of the orthostatic hypotension.

41. A programmable cardiac stimulation device having a memory and a processor, the cardiac stimulation device being programmed to perform tasks comprising:

administering pacing therapy to a patient when the device (1) detects a postural change from a horizontal position to an upright position and (2) confirms the postural change using a cross-check parameter; and subsequently removing the pacing therapy in a systematic manner.

42. The programmable cardiac stimulation device of claim 41, wherein the cross-check parameter comprises an evoked response amplitude.

43. The programmable cardiac stimulation device of claim 41, wherein the cross-check parameter comprises a cross-check parameter is selected from a group of parameters comprising stroke volume, a cardiac impedance parameter, evoked response integral, ventricular wall thickness, ventricular pressure, atrial evoked response amplitude, and atrial evoked response integral.

44. The programmable cardiac stimulation device of claim 41, wherein the cardiac stimulation device is programmed to perform additional tasks comprising:

monitoring an evoked response parameter (ERP) functionally related to an evoked response amplitude (ERA);

computing a delta ERP ($\Delta$ERP) as a function of the ERP and a moving average of the ERP;

examining the $\Delta$ERP computed at approximately at time when the postural change is detected; and in an event that the $\Delta$ERP changes by a predetermined amount, confirming that the postural change did occur.

* * * * *